United States Patent [19]

Basta

[11] 4,022,219
[45] May 10, 1977

[54] ENDOTRACHEAL DEVICE

[76] Inventor: Edward Basta, 300 N. State St., Suite 4930, Chicago, Ill. 60610

[22] Filed: July 28, 1975

[21] Appl. No.: 599,534

[52] U.S. Cl. .............................................. 128/351
[51] Int. Cl.² ...................................... A61M 25/00
[58] Field of Search ......................... 128/348–351, 128/276–278, 208, 145.5, 4–8

[56] References Cited

UNITED STATES PATENTS

| | | | |
|---|---|---|---|
| 1,286,083 | 11/1918 | Pennington | 128/6 |
| 2,162,681 | 6/1939 | Ryan | 128/6 |
| 2,614,563 | 10/1952 | Devine | 128/276 |
| 2,705,959 | 4/1955 | Elmore | 128/351 |
| 2,912,982 | 11/1959 | Barsky | 128/351 |
| 3,297,027 | 1/1967 | Rusch | 128/351 X |
| 3,730,179 | 5/1973 | Williams | 128/145.5 |
| 3,815,606 | 6/1974 | Mazal | 128/351 |
| 3,833,003 | 9/1974 | Taricco | 128/347 |

*Primary Examiner*—Dalton L. Truluck
*Attorney, Agent, or Firm*—Wegner, Stellman, McCord, Wiles & Wood

[57] ABSTRACT

An endotracheal device is provided with a double lumen, one for the passage of oxygen and the other for use in catheterizing or suctioning a patient. The device comprises an endotracheal tube connected to an adaptor which adaptor has connectors for connecting one lumen or passageway to a source of oxygen and for connecting the other lumen or passageway to a source of suction. The device can be used to aspirate and to oxygenate a patient separately or simultaneously.

8 Claims, 4 Drawing Figures

U.S. Patent      May 10, 1977      4,022,219
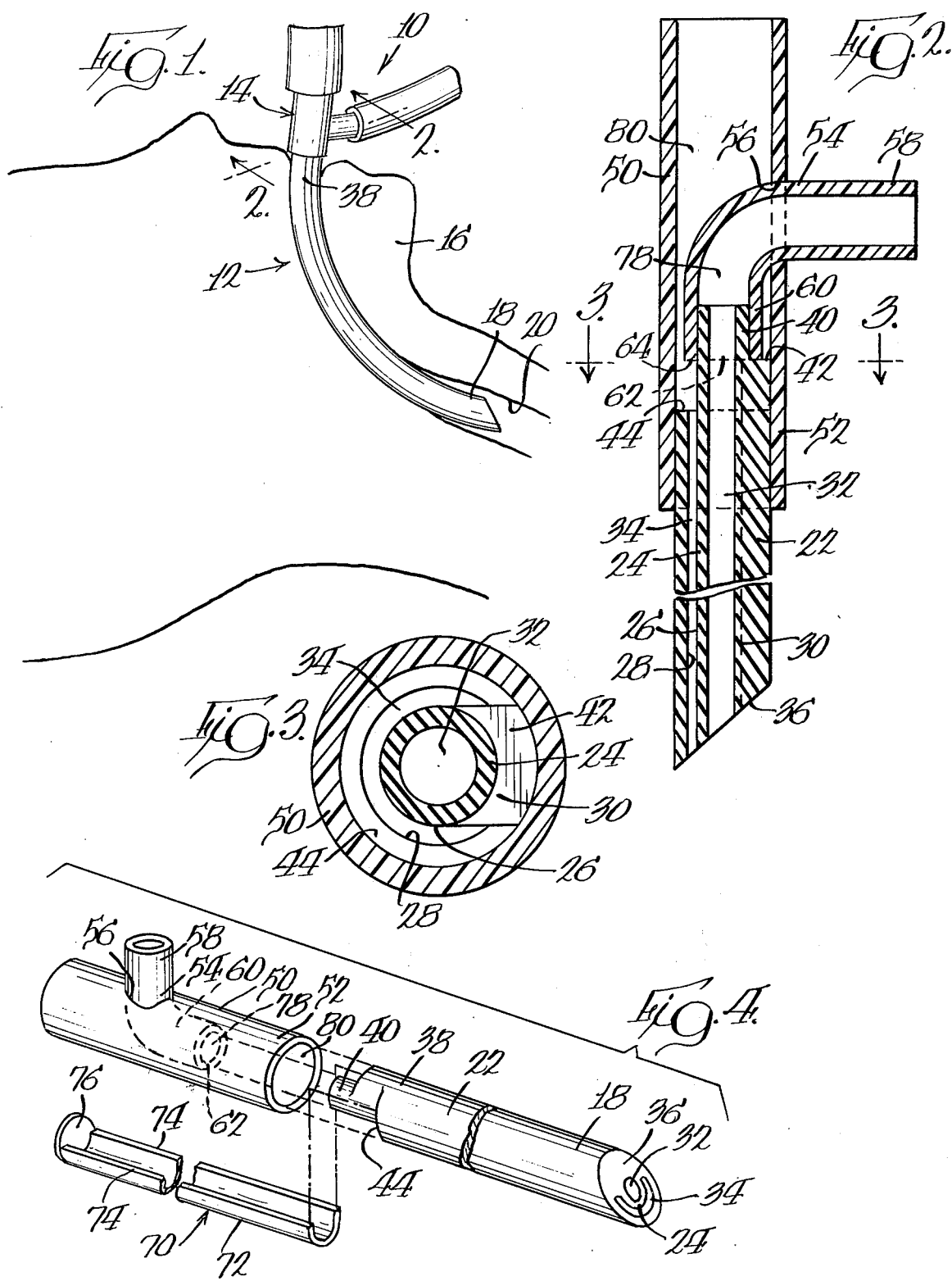

_4,022,219_

ENDOTRACHEAL DEVICE

BACKGROUND OF THE INVENTION

1. Field of the Invention

This invention relates to the medical instrumentation field and, more particularly, to an endotracheal device having a double lumen for use in not only administering oxygen to a patient, but also to aspirate the patient.

2. Description of the Prior Art

Currently available endotracheal tubes are comprised of a plastic flexible cannula which, when used by experienced and properly trained personnel, is inserted through the larynx and through the vocal chords and is lodged well beyond into the tracheal canal. To assist in placing the tube, a stylet is provided in the cannula to confer proper rigidity thereto so as to permit the tube to be forcibly inserted through the larynx and the vocal chords. Once the endotracheal tube is in place, the stylet is removed and the proximal end of the tube is connected with a positive pressure oxygen pumping device, thus allowing direct and theoretically infallible conveyance of oxygen to the patient's lungs.

The endotracheal tube is mainly used in all cases where resuscitating procedures are of the utmost immediate and manditory necessity for survival of the patient. Therefore, the endotracheal tube is considered an emergency or lifesaving device. The endotracheal tube is used routinely and commonly in anesthesiology for every surgical and sometimes for non-surgical patients.

Up to the present time, especially where the tube is used to save the life of a sudden cardiac arrest, often ensuing from an acute myocardial infraction, the intubation of the patient and subsequent administration of oxygen may prove inadequate, particularly if the lungs of the patient are filled or are filling with edematous fluids, mucus and other pulmonary secretions, or even blood as in the case of a chest injury. Unfortunately, due to the buildup of fluids in the lungs, any attempt to administer oxygen must be interrupted to allow suctioning of the fluids from the lungs. This means that the oxygen must be disconnected and a catheter must be introduced through the endotracheal tube and connected to a suctioning machine whereby aspiration of the lung clogging fluids can take place. Such aspiration of the fluids, unfortunately, can only be implemented for a few seconds and, therefore, is never adequate because it is necessary to remove the catheter and immediately go back on oxygen to prevent compromising the blood flow oxygenation to the brain's vital centers. The unfortunate result of most of these situations requiring alternating between the insertion of the secretion removing catheters and the oxygenating procedures, is the overflowing of the pulmonary edematous secretions into the lungs fatally preventing any oxygen at all from reaching the lungs.

It is with this extremely serious problem in mind that the present invention was conceived.

SUMMARY OF THE INVENTION

Broadly stated, my invention is directed to a device whereby a patient may be simultaneously or sequentially administered oxygen while pulmonary edematous secretions are aspirated from the lungs. My endotracheal device consists of an endotracheal tube having a double lumen or two passageways therein, one lumen or passageway being for use in administering oxygen and the other lumen or passageway being used for aspirating and withdrawal of fluids from the patient and a multiported adaptor which has two connecting portions, one for connection to a source of oxygen and the other for connection to a source of vacuum for withdrawal of fluids. By use of my improved endotracheal device, it is possible to either separately or simultaneously oxygenate a patient and at the same time aspirate and withdraw fluids from the patient.

The endotracheal tube with the double lumen has one central lumen of larger cross-sectional capacity than the other partial peripheral lumen which has reduced cross-sectional capacity. The peripheral lumen is only partially circular in that the central lumen is connected or anchored to the side of the cannula of the tube. For placing the endotracheal tube, a metal guide or stylet is provided which nests in the outer peripheral lumen, which guide or stylet adds rigidity to the tube to assist in placing the tube in the patient. The metal guide or stylet is then removed and a multiported adaptor is affixed to the tube such that the inner circular lumen communicates with a sidewardly extending port from the adaptor and the outer peripheral lumen communicates with the in line opening or port in the adaptor. By applying a vacuum to the sidewardly extending port of the adaptor, fluids are drawn from the patient through the circular lumen. By applying oxygen under pressure through the other port in the adaptor, oxygen is administered to the patient.

Using my improved endotracheal device, it is possible to both aspirate and oxygenate a patient separately or simultaneously.

The endotracheal tube is disposable, while the adaptor is a permanent item kept in the appropriate area of the hospital or clinic.

BRIEF DESCRIPTION OF THE DRAWINGS

The details of construction and operation of the invention are more fully described with reference to the accompanying drawings which form a part hereof and in which like reference numerals refer to like parts throughout.

In the drawings:

FIG. 1 shows an endotracheal device made in accordance with the invention and comprises an endotracheal tube and an adaptor;

FIG. 2 is a cross-sectional view taken along the lines 2—2 of FIG. 1;

FIG. 3 is a cross-sectional view taken along the lines 3—3 of FIG. 2; and

FIG. 4 is an exploded perspective view of the invention showing the endotracheal tube aligned with the adaptor and with the insertion stylet offset therefrom.

DESCRIPTION OF THE PREFERRED EMBODIMENT

Referring in detail to the drawings, and in particular to FIG. 1, an endotracheal device 10 is shown and comprises an endotracheal tube 12 and an adaptor 14, the endotracheal tube 12 in position through the mouth of a patient 16 and past the larynx and vocal chords with the distal end 18 positioned downstream from the vocal chords in the trachea 20 of the patient.

As best seen in FIGS. 2, 3 and 4, the endotracheal tube 12 is molded, extruded or otherwise formed, from medical grade plastic material having semiflexible characteristics. The tube has an outer cannula 22 with a tubular inner cannula 24 extending throughout the length of the inside thereof with a part of the outside wall 26 of the inner cannula 24 being joined to a part of the inner wall 28 of the outer cannula 22. The connection or junction 30 between the outside wall of the inner cannula 24 and the inner wall of the outer cannula 22 is illustrated as a solid connection. The cannula 24 has a lumen 32 extending throughout the length thereof. It is contemplated that in making the endotracheal tube, the inner tubular cannula 24 and the outer cannula 22 could be formed simultaneously with the wall of the cannula 24 connected to the wall of the cannula 22 as an integral part. With the inner tubular cannula 24 extending throughout the central portion of the cannula 22 and joined at 30 thereto, a somewhat U-shaped lumen 34 is provided between the inner surface of the cannula 22 and the outer surface of the cannula 24 where the two overlap each other throughout the length of the cannula 22. The relative sizes of the lumen 32 in the cannula 24 and 34 in the cannula 22 is such that the cross-sectional capacity of lumen 32 is larger than the cross-sectional capacity of lumen 34. That is, the lumen 32 has a larger cross-sectional area than the cross-sectional area of lumen 34 so that more fluid, i.e. secretions or blood, could flow through lumen 32 than could flow through lumen 34. The distal end portion 18 of the tube 12 has an end wall 36 formed at an angle to the axis of the tube 12 so as to assist in guiding the endotracheal tube into position in the trachea of a patient. The angular relationship of the end wall 36 to the axis of the tube is well known in the art.

The proximal end portion 38 of the endotracheal tube 12 has the inner cannula 24 projecting longitudinally therefrom a short distance to form a male connection or nipple 40 beyond a shoulder 42 which is formed by the end of the cannula 22 and the end wall of the connection or junction 30 joining the inner wall of the cannula 22 with the outer wall of the cannula 24. The shoulder 42 lies in a plane substantially perpendicular to the longitudinal axis of the endotracheal tube. Spaced axially from the shoulder 42 is the end wall 44 of the cannula 22.

The adaptor 14 is comprised of a tubular sleeve 50 with a distal end portion 52 which has an inside diameter of a size to slip-fit over the outside diameter of the cannula 22 of the endotracheal tube 12. An L-shaped tubular member 54 passes through an opening 56 in the wall of the tubular sleeve 50 with one leg of the "L" projecting externally of the sleeve 50 with the other leg 60 projecting axially on the inside of the sleeve 50 with an open end 62 facing the distal end 52 of the sleeve 50. The L-shaped tubular member 54 has the leg 58 permanently secured in the opening 56, such as by means of heat sealing or the like. The open inner end 62 of the leg 60 of the member 54 has an internal diameter which is adapted to slip-fit over the outer surface of the male connection or nipple 40 projecting proximally from the endotracheal tube 12.

When the adaptor 14 is assembled with the endotracheal tube 12, the nipple 40 on the inner cannula 24 and the outer surface of the cannula 22 are aligned with and inserted into the distal end portion 52 of the adaptor 14. The nipple 40 on cannula 24 slides into the end portion of leg 60 of the L-shaped member 54 until the end wall 64 of the leg 60 abuts against the shoulder 42 on the endotracheal tube 12. As the nipple 40 slides in the leg 60, the distal end portion 52 of the sleeve 50 is sliding over the proximal end portion of the cannula 22. When the wall 64 abuts the shoulder 42, the adaptor is assembled with the endotracheal tube and the endotracheal device is ready for use. The fit between the sleeve 50 and the cannula 22, and between the nipple 40 and the leg 60 are snug and fluid tight. It is to be noted that with the adaptor 14 assembled with the tube 12, the end wall 64 abuts shoulder 42 but is also spaced from the end wall 44 of the main cannula 22 so as not to obstruct free access to the open end of the U-shaped lumen 34.

To assist in placing the endotracheal tube 12 in the trachea 20 of a patient 16, prior to the assembly of the adaptor 14 to said tube 12, a guide or stylet 70 is provided and is assembled with the endotracheal tube so as to add rigidity to the tube. Specifically, the guide or stylet 70 has a body portion 72 which is semi-circular in cross section and has a length substantially equal to the length of the main portion of the endotracheal tube 12. The diameter of the semi-circular cross section of the body portion 72 is such as to conform to the internal diameter of the U-shaped lumen 34 in the cannula 22. The upwardly projecting surfaces 74 of the body portion 72 will face the closed portion of the junction 30 between the inner cannula 24 and the outer cannula 22 so that the stylet or guide 70 will conform to the nest in the U-shaped lumen 34 in the cannula 22. The distal end of the guide or stylet 70 has an end cap or handle 76 welded or otherwise secured over the end portion thereof. The purpose of the handle 76 is that when the guide or stylet 70 is pushed in position in the lumen 34 of the cannula, the handle 76 will engage against the end surface of the nipple 40 of the cannula 24 so that pressure on the handle 76 and on the tube 12 will apply pressure throughout the length of the endotracheal tube 12 with the body portion 72 of the guide or stylet 70 serving as a backbone or stiffening member for the endotracheal tube 12, making it possible to force the distal end of the endotracheal tube past the larynx and vocal chord and into the downstream portion of the trachea of the patient. Once the tracheotomy tube 12 is in position in the patient, the guide or stylet 70 is removed from the lumen 34 of the endotracheal tube 12 and the adaptor 14 is assembled with the tube. That is, the distal end portion 52 of the adaptor is inserted over the proximal end portion of the endotracheal tube with the leg 60 of the L-shaped member 54 engaging with the nipple 40 on the cannula 24 so that the passageway or lumen 78 in the member 54 communicates with the passageway or lumen 32 in the cannula 24. The U-shaped lumen 34 in the cannula 22 communicates with the lumen 80 on the inside of the sleeve 50 of the adaptor and is in communication with the open proximal end of the sleeve 50.

An external source of vacuum is connected to the leg 58 of the L-shaped member 54 so that a vacuum or suction can be drawn through the larger lumen 32 of the tube 12. A source of oxygen under pressure is connected to the end portion of the sleeve 50 so that oxygen supplied under pressure is fed through the interior of the sleeve 50 and around the L-shaped member 54 and through the U-shaped lumen 34 in the cannula 22 of the endotracheal tube 12. The U-shaped lumen 34 opens through the end wall 36 of the tube 12 so that oxygen forced therethrough will be fed from the endotracheal tube into the trachea 20 of the patient. Edematous secretions that buildup in the lungs of the patient, can be aspirated through the lumen 32 by means of a suction or vacuum drawn on the member 54. In this way, the patient can be administered oxygen continuously or as needed and when the patient begins to develop excesses of the edematous secretions, the secretions may be withdrawn by applying a vacuum or suction through the member 54 and through the lumen 34 of the cannula 24. The patient can simultaneously receive oxygen through the lumen 32 and have the secretions aspirated or withdrawn from the lungs by the suction being drawn through the lumen 34. The patient can be receiving oxygen and be having fluids drawn out of the chest cavity simultaneously or sequentially, as required. Using the improved device, it is not necessary to remove the connecton to the oxygen source so that a catheter can be threaded through the endotracheal tube upon which suction is applied to withdraw secretions that have built up in the lung cavity. The rapid switching from use of the endotracheal tube for administering oxygen and then converting the endotracheal tube for threading a catheter for evacuating fluids with all the attended complications associated therewith is completely avoided with my improved endotracheal device.

After the patient has recovered sufficiently, the endotracheal device can be removed from the patient and the endotracheal tube 12 removed from the adaptor 14 with the endotracheal tube 12 being discarded and the adaptor 14 being cleaned and sterilized for subsequent use with another patient or with the same patient, as the case may be.

It is contemplated that under certain circumstances, a narrow gauge catheter may be threaded through the lumen 78 in the member 54 and the lumen 32 in the cannula 24 so that the end of the catheter can be positioned deeper in the tracheal cavity for extracting secretions from the patient. In the cases where the additional catheter is threaded through the cannula 24 with the distal end of the catheter deeper in the patient's tracheal cavity, the proximal end of the catheter is attached to the vacuum source for aspirating the secretions. It is believed to be clear that the endotracheal device with the use of an additional catheter for deeper catheterization for the patient, still provides the dual function for my construction, wherein a patient may simultaneously be given oxygen and at the same time have secretions aspirated through a separate catheter.

From the above description, it can be seen that I have provided an improved endotracheal device that makes it possible to administer oxygen to a patient simultaneously with or separately from aspirating fluids from the patient, all through the same endotracheal tube and without the need for interrupting one or the other while performing either. The improved endotracheal device is a lifesaving apparatus that makes it possible to assist in saving many patients' lives.

In order to prevent the oxygen being administered through opening 34 from being sucked immediately into the end of the suction tube 32 during simultaneous suctioning of fluids and administering of oxygen, the length of the inner tube is modified with respect to the length of the outer tube.

I claim:

1. An endotracheal tube comprising a tubular member having a proximal end, a tapered distal end and two lumen connecting said ends for transport of oxygen to and aspirating fluid from the body of a patient, the first of said lumen being formed by an elongate cannula secured along a longitudinal side thereof to the inside wall of said tubular member and terminating at the short end of the tapered distal end of said tube, said cannula having an outside diameter less than the inside diameter of said tubular member whereby the second of said lumen is defined by the space between said cannula and said tubular member and terminates at the long end of said tapered end of said tube, the cross-sectional area of said second of said lumen is smaller than the cross-sectional area of said first of said lumen, an adaptor having a member connected to said lumen in said cannula for connecting said lumen in said cannula to a source of suction, said adaptor having a sleeve connected with said tubular member with the lumen in said sleeve communicating with the lumen in the tubular member for connecting said second lumen to a source of oxygen under pressure whereby the patient may be administered oxygen through the second lumen at an axially spaced location from the inlet of fluids being aspirated from the body through the first lumen.

2. An endotracheal tube as claimed in claim 1 wherein a stylet which is U-shaped in cross section in a plane perpendicular to the longitudinal axis of said stylet is provided for insertion in said second lumen to add stiffness to said tube during placing said tube in the trachea of a patient.

3. An endotracheal device as claimed in claim 1 wherein said adaptor is removable from said endotracheal tube, said endotracheal tube being disposable and said adaptor being disposable and said adaptor being sterilizable for reuse.

4. An endotracheal device having an endotracheal tube and an adaptor for connection to a source of vacuum and to a source of oxygen under pressure, said endotracheal tube comprising a plastic body member having two lumen extending from a distal end to a proximal end thereof, the distal end of said tube lying in a plane disposed at an angle to the axis of said tube with both of said lumen terminating in said plane, said body member has a cannula seated therein, the inside of said cannula forming one of said lumen, the space between said cannula and the inside of said tubular member forming the second lumen, the cross-sectional area of the inside of said cannula being larger than the cross-sectional area between said cannula and the inside of said tubular member, said adaptor having two lumen therein with one lumen being connectable to a source of vacuum and the other lumen being connectable to a source of oxygen under pressure, said endotracheal tube being attachable to said adaptor with the two lumen of said tube communicating with the two lumen of said adaptor whereby said endotracheal device is adapted for use simultaneously for withdrawing fluids from a body and for administering oxygen to a body.

5. An endotracheal device as claimed in claim 4 wherein said adaptor comprises a sleeve sealingly engageable with the body member of said tube, a hollow L-shaped member carried by said sleeve with one end sealingly engageable with said cannula, said sleeve being connectable to said source of oxygen and said L-shaped member being connectable to a source of vacuum.

6. An endotracheal tube including an elongate tubular cannula formed of semiflexible plastic material, said tube having a distal end wall lying in a plane forming an angle with respect to the axis of said tube, means in said cannula for forming two lumen extending the length of said cannula with each lumen terminating in said distal end wall of said tube, said means comprising a second tubular cannula with a smaller outside diameter than the inside diameter of said first-named tubular cannula, means for securing said second tubular cannula in said first-named tubular cannula whereby one lumen is in the second tubular cannula and the other lumen is between said second tubular cannula and the inside of said first-named tubular cannula, said one lumen in the second tubular cannula is larger in cross-sectional area so as to accommodate a higher rate of flow of fluids therethrough, means for attaching said one lumen in the second tubular cannula to a source of suction, the other lumen with the smaller cross-sectional area being attachable to a source of oxygen under pressure whereby oxygen can be administered through the said other lumen of the tube at the same time fluids may be aspirated through the lumen in the second tubular cannula.

7. An endotracheal tube as claimed in claim 6 wherein an adaptor is provided for connection to a proximal end of said tube, said adaptor having a sleeve connected with said other lumen and with a source of oxygen, and said adaptor having a member connected with a nipple on said second tubular cannula and with a source of suction.

8. An endotracheal tube as claimed in claim 6 wherein a stylet which is U-shaped in cross section is provided for threading into the lumen between said second tubular cannula and the inside of said first-named tubular cannula for adding stiffness to said cannula as the tube is inserted in place in a patient, said stylet being removable before connecting the two lumen of said tube to said oxygen and to said vacuum.

* * * * *